(12) United States Patent
Nazzer

(10) Patent No.: US 8,652,304 B2
(45) Date of Patent: Feb. 18, 2014

(54) PROCESS FOR SEPARATING SOLIDS FROM VALUABLE OR HARMFUL LIQUIDS BY VAPORISATION

(75) Inventor: Craig Nazzer, New Plymouth (NZ)

(73) Assignees: Prime Services Trustee Limited, New Plymouth (NZ); VBW Trustees No. 2 Limited, New Plymouth (NZ)

( * ) Notice: Subject to any disclaimer, the term of this patent is extended or adjusted under 35 U.S.C. 154(b) by 393 days.

(21) Appl. No.: 12/997,717

(22) PCT Filed: Jun. 15, 2009

(86) PCT No.: PCT/NZ2009/000103
§ 371 (c)(1),
(2), (4) Date: Dec. 13, 2010

(87) PCT Pub. No.: WO2009/154477
PCT Pub. Date: Dec. 23, 2009

(65) Prior Publication Data
US 2011/0094871 A1   Apr. 28, 2011

Related U.S. Application Data

(60) Provisional application No. 61/061,644, filed on Jun. 15, 2008.

(51) Int. Cl.
*C07C 41/38*   (2006.01)
*C07C 27/28*   (2006.01)

(52) U.S. Cl.
USPC ............. 203/18; 159/2.1; 159/47.3; 159/901; 203/78; 203/79; 203/80; 203/88; 203/93; 203/94; 203/96; 203/97; 203/98; 210/712; 210/737; 568/913

(58) Field of Classification Search
USPC ............ 159/2.1, 44, 47.3, 901; 203/1, 18, 78, 203/79, 80, 88, 92–98; 210/712, 737; 568/913
See application file for complete search history.

(56) References Cited

U.S. PATENT DOCUMENTS

| | | | |
|---|---|---|---|
| 2,976,224 A |   | 3/1961 | Gilliland |
| 3,976,742 A | * | 8/1976 | Blanco et al. ................... 423/24 |
| 4,133,740 A | * | 1/1979 | Paraskos et al. ................ 208/45 |
| 4,289,578 A | * | 9/1981 | Greenfield et al. .......... 159/47.3 |
| 4,315,815 A | * | 2/1982 | Gearhart ....................... 208/321 |
| 5,441,605 A | * | 8/1995 | Beasley et al. ................ 202/176 |
| 5,993,608 A | * | 11/1999 | Abry et al. ....................... 203/11 |
| 6,685,802 B1 | * | 2/2004 | Nazzer ............................. 203/1 |

FOREIGN PATENT DOCUMENTS

GB         1502323  A    3/1978

OTHER PUBLICATIONS

International Search Report in PCT/NZ2009/000103 mailed Aug. 11, 2009.

* cited by examiner

*Primary Examiner* — Virginia Manoharan
(74) *Attorney, Agent, or Firm* — Mossman Kumar & Tyler PC

(57) ABSTRACT

The present invention is directed to an enhanced process for separating dissolved and suspended solids from valuable or harmful liquids and more particularly to improving the operational aspects and separation efficiency of treating certain water miscible fluids including those used for oil and gas processing such as glycols, as well as automobile and aircraft fluids, that have become contaminated with dissolved and/or suspended solid matter.

6 Claims, 2 Drawing Sheets

PROCESS FOR SEPARATING SOLIDS FROM VALUABLE OR HARMFUL LIQUIDS BY VAPORISATION

RELATED APPLICATIONS

This application claims priority to International Application No. PCT/NZ2009/000103 filed 15 Jun. 2009, which claims the benefit of U.S. Provisional Patent Application No. 61/061,644 filed on 15 Jun. 2008, which applications are hereby incorporated by reference herein, in their entirety.

FIELD OF THE INVENTION

The present invention is directed to a novel process for separating dissolved and suspended solids from valuable or harmful liquids. In particular aspects, the invention relates to improved and efficient methods for treating water miscible fluids that have become contaminated with dissolved and/or suspended solid matter. These include fluids used for oil and gas processing, as well as fluids used in automobile and aircraft systems, among others.

BACKGROUND OF THE INVENTION

Water miscible liquids such as glycols are used in oil and gas production but can become contaminated with dissolved and/or suspended solid matter. Rather than discarding the contaminated liquid, it is generally preferable to remove the solid matter so as to regenerate and reuse the liquid. At many locations worldwide, dissolved salts and other similar contaminating substances are separated from the process liquid (e.g. glycol) by vacuum flash vaporisation processes. Examples of such processes are disclosed in U.S. Pat. Nos. 5,993,608, 6,340,373; 6,508,916, and 6,685,802, incorporated herein by reference, as well as other publications. Industrial plants that apply the flash vaporisation process to glycol are currently in design, under construction, or in operation in the USA, UK, Norway, Brazil, Canada, New Zealand, Australia, India, Russia, Egypt, Azerbaijan, and other countries.

At oil and gas production facilities, the fluids that come from the oil and gas wells may contain substantial amounts of formation water. This, in turn, contains salts and other unwanted substances. At these facilities, mono-ethylene glycol is injected into hydrocarbon flow lines to prevent the formation of hydrates that can plug pipelines. The water then mixes with the glycol to form a dilute aqueous glycol solution. When the crude hydrocarbons are collected at the oil and gas production plant, the dilute aqueous glycol solution is separated from the hydrocarbon fluids. It is then reconcentrated by boiling off excess water, and transported back upstream to be reinjected into the flow lines. In this way, the glycol is reused many times. However, in the absence of treatment, it accumulates unwanted non-volatile solid matter with each recycling round.

The salts and other solid matter can build-up until the level of contamination in the glycol causes increased corrosion, rapid thermal degradation of the glycol, unwanted precipitation of solid matter, fouling of heat transfer equipment and other serious, costly, operational problems. Chlorides, oxides, sulfates, bicarbonates, and carbonates of sodium, potassium, calcium, magnesium, iron, barium, and strontium are examples of inorganic contaminants. Sodium chloride is generally the most prevalent inorganic contaminant. A major source of the salts and other solid matter is the formation water that flows with the hydrocarbon fluids out of the oil and gas production wells. Another source can be the brines and other completion fluids that are injected into the flow lines during or after exploration to prepare for initial production, or as a result of well maintenance activities. Other potential sources include the products of corrosion of the flow lines and the chemicals injected into the flow lines to control corrosion. These non-volatile contaminants must be removed to maintain the quality of the glycol and efficient operations when the glycol is regenerated and reused.

In facilities that treat glycol using a flash vaporisation process, a feed stream comprising an aqueous glycol solution containing contaminants such as dissolved salts is caused to boil rapidly upon mixing with a heated recycle fluid within or in proximity to a flash separation vessel, hereinafter termed the Flash Separator. The vapors that flow out the top of the Flash Separator are depleted of contaminants. Typically, these vapors are either condensed or further separated by distillation into water and concentrated process liquid. The process is normally run under vacuum at an absolute pressure of 0.1 to 0.4 bara so as to reduce the operating temperature when treating a thermally sensitive process liquid such as glycol. Most of the dissolved contaminants, such as sodium chloride, precipitate and fall into a pool of liquid in the lower part of the Flash Separator. The liquid in this pool is a more concentrated solution of the glycol in equilibrium with the vapor phase at about 100 to 150° C. This liquid contains high levels of contaminants in the form of precipitated salt crystals, dissolved inorganic ions and suspended particles. A recycle fluid is drawn from this pool of concentrated glycol in the Flash Separator, heated, and then mixed with the feed stream as described above.

Conventional flash vaporisation process plants typically include additional equipment such as centrifuges, settling tanks or filters to separate the precipitated and suspended solids from the pool of concentrated process liquid in the Flash Separator. The solids are typically then disposed of. These added equipment items have a number of disadvantages such as complexity and high capital cost (centrifuges, filtration), large weight and footprint (settling tanks, filtration), high loss of process liquid with the waste solid matter, and high costs to prevent release of large amounts of process liquid into the environment. These problems are amplified if the flash vaporisation process plant is located on an offshore structure because the use of the added separation equipment described above leads to higher loads on the supporting structure, loss of space, discharge of harmful substances to the ocean, and/or added costs for transport of materials or personnel to/from shore.

In the Flash Separator, sodium, chloride and many other similar dissolved salts precipitate in the form of distinct solid particles, capable of settling, of typically 20 to 100 micron size. However calcium and some other divalent cations are an exception. If the feed stream contains significant quantities of calcium, then in the absence of extra treatment, the calcium accumulates in the recycle fluid. Dissolved calcium, if present, does not precipitate to form well behaved particles in the concentrated glycol. Instead, it combines with glycol and chloride to form calcium-glycol-chloride complex compounds that raise the viscosity of the recycle fluid and solidify if allowed to cool to less than about 100 to 120° C. Over time, as more calcium builds up, the recycle fluid viscosity can become unmanageable. Then, upon cooling, the entire mass of liquid in the Flash Separator can turn solid. This has been a costly experience at several operating plants. Other divalent cations can also cause a similar effect. However, most research and plant design work has focused on finding a solution for calcium, as it is typically the most prevalent divalent cation. The presence of calcium in formation water is not surprising given that it is a major component of limestone and other subsurface rock found in some oil and gas fields.

Plant designers have sought to address the calcium problem by including an additional treatment procedure. This treatment starts by mixing a carbonate containing material, such as an aqueous solution of sodium carbonate, with the incoming glycol upstream of the flash vaporisation process. The calcium ions combine with the added carbonate to form insoluble calcium carbonate which is then mechanically removed in clarifiers and/or filters. This solution has been in use since at least 1994. There are several major drawbacks with this treatment procedure, including: the cost and complexity of adding carbonate to the glycol; the size, cost and complexity of the carbonate filtration equipment; and the high glycol content in the waste solid material. As before, these problems are amplified if the equipment used in the calcium treatment procedure described above is located on an offshore structure because this leads to; higher loads on the supporting structure, loss of space, discharge of harmful substances to the ocean, and/or added costs for transport of materials or personnel to/from shore.

Other less common contaminants have been known to, or have been identified by researchers as having the potential to, cause problems with the flash vaporisation process when used to treat glycol. Three examples are acetate, nitrate and phosphate which can dissolve in glycol and cause undesirable changes to the properties of the recycle fluid.

Thus, there is a need in the art for an improved method for treating water miscible process liquids, for example, fluids used for oil and gas processing, that have become contaminated with dissolved and/or suspended solid matter.

SUMMARY OF THE INVENTION

In one aspect, the present invention provides a process of extracting solids, which are dissolved or undissolved, from a mixture of water and a process liquid, said process including the steps of:
  placing an oil or oil-like recycle source liquid that is less dense than water, and is comprised of components that are substantially non-miscible with and less volatile than water and less volatile than the process liquid, into a separation vessel;
  introducing a feed stream comprising a mixture of water, the process liquid and the solids to be extracted into a mixing zone in proximity to or within the separation vessel;
  rapidly boiling or flashing the feed stream upon mixing the feed stream with a recycle fluid in the mixing zone to produce a vapor in proximity to or within the separation vessel;
  separating the vapor from the unvaporised components of a mixture of the feed stream and the recycle fluid;
  collecting the unvaporised components in a substantially liquid pool in a lower portion of the separation vessel;
  drawing the recycle fluid from the substantially liquid pool at a rate that is more than ten times the feed stream flow rate;
  pumping the recycle fluid through a heat exchanger;
  supplying sufficient heat to the recycle fluid in the heat exchanger such that the amount of heat added to the recycle fluid is sufficient to vaporise volatile components of the feed stream when the recycle fluid and the feed stream are mixed in the mixing zone;
  allowing at least a portion of the solids in the substantially liquid pool and at least a portion of any liquid bound thereto to move into a stripping zone and come into contact with water contained therein;
  allowing at least a portion of the solids that has moved into the stripping zone to move through at least a portion of the water in the stripping zone;
  wherein the passage of the portion of the solids through the portion of the water displaces at least a portion of any other liquid bound to the portion of the solids; and
  removing from the stripping zone a waste aqueous stream containing at least a portion of the solids that have entered the stripping zone.

The invention can be further modified by one or more of the following steps:
  some or all of any vaporised components of the recycle fluid are condensed and returned to the liquid pool in the lower portion of the separation vessel;
  the stripping zone is connected to the bottom of the separation vessel and at least a portion of the solids from the liquid pool fall by gravity out of the liquid pool and into the stripping zone;
  water is added to the stripping zone to displace the waste aqueous stream; and
  the separation vessel is operated at between 0.03 and 0.50 bara to avoid thermal degradation of thermally sensitive process liquids.

In one aspect, the present invention provides an apparatus for extracting solids, which are dissolved or undissolved, from a mixture of water and a process liquid, the apparatus comprising:
  a reservoir A, comprising an upper part and a lower part, in which the upper part includes a vapor-liquid separation zone, and the lower part includes a liquid pool zone that holds in use an oil or oil-like recycle source liquid, wherein the recycle source liquid is less dense than water, and is comprised of components that are substantially non-miscible with and less volatile than water and less volatile than the process liquid;
  a conveying means for moving a feed stream comprising a mixture of water, the process liquid, and the solids to be extracted, into a reservoir B that contains a mixing zone;
  a conveying means for extracting a recycle fluid from the liquid pool zone in reservoir A and moving the recycle fluid into the mixing zone in reservoir B;
  a heating means for supplying sufficient heat to the recycle fluid before it enters the mixing zone in reservoir B such that the amount of heat added to the recycle fluid is sufficient to vaporise volatile components of the feed stream when the recycle fluid and the feed stream are mixed in the mixing zone in reservoir B;
  a conveying means for moving vapor from the mixing zone in reservoir B, through the vapor-liquid separation zone in reservoir A, and out of reservoir A;
  a conveying means to enable the solids and other unvaporised substances to move from the mixing zone in reservoir B, through the vapor-liquid separation zone in reservoir A and into the liquid pool zone in reservoir A;
  a reservoir C to hold in use water within a stripping zone in reservoir C;
  a conveying means in proximity to the lower part of reservoir A for bringing at least a portion of the solids in the liquid pool zone in reservoir A and at least a portion of any liquid bound thereto, into contact with the water in the stripping zone in reservoir C;
  a conveying means to move at least a portion of the solids that have entered the stripping zone in reservoir C and at least a portion of the liquid bound thereto through at least a portion of the water in the stripping zone in reservoir C wherein movement displaces at least a portion of any other liquid bound to the solids; and a conveying means to remove at least a portion of the solids from reservoir C.

In particular aspects, the invention can be used in plants which treat glycols, amines or other water miscible fluids that have become contaminated with dissolved and/or suspended solid matter.

In certain aspects, the stripping step is optional or is performed in a different apparatus, or at a different facility.

It is to be appreciated that this invention can be applied to treat many fluids that contain glycol or similar liquids including engine antifreeze/coolant, aircraft de-icing fluid and other similar fluids and in circumstances that do not involve oil and gas production.

It is also possible to use the treatment of the invention in a continuous manner.

Further aspects of this invention which should be considered in all its novel aspects will become apparent from the following description given by way of example of possible embodiments thereof, and in which reference is given to the accompanying drawings.

DETAILED DESCRIPTION OF THE INVENTION

It is an object of the present invention to substantially simplify and reduce the cost of the processes used to separate solids from a process liquid such as glycol used in oil and gas production. In so doing, the invention avoids or minimises the following problems: the release of harmful or valuable process liquid into the environment; the purchase of new process liquid to replace what was lost with the waste solids; the severity of operational problems caused by the interaction of some types of inorganic ions with the process liquid and the extent of supplementary chemical treatment needed to mitigate these problems; and the cost and complexity of equipment and systems to recover process liquid from the waste solid material.

It is an additional object of the invention to at least provide the public with a useful alternative to available methods.

While certain aspects of the invention relate to process liquids such as glycol, for example, mono-ethylene glycol, which are used in oil and gas production, the invention is useful for other water miscible liquids that are contaminated by dissolved and/or suspended solid matter. These include amines, engine antifreeze, engine coolant, aircraft de-icing fluid, among others.

In certain aspects of the invention, the recycle fluid comprises an oil or oil like liquid. In other aspects, the recycle fluid comprises an ionic liquid, in which case it exhibits almost no vapor pressure. In accordance with this aspect, there is essentially no vaporised recycle fluid leaving the separation vessel, and the recycle fluid is contained within the separation vessel.

The invention can be used for a wide range of dissolved and/or suspended solid matter, for example, chlorides (e.g., sodium chloride), oxides, sulfates, acetates, nitrates, phosphates, bicarbonates and carbonates of sodium, potassium, calcium, magnesium, iron, barium, and strontium. The invention is particularly useful for removing calcium and other divalent cations, such as magnesium, strontium, barium, copper, and lead.

Table 1 below presents non-limiting examples of dissolved inorganic ion content encountered in the formation water in a number of gas producing areas in the world.

TABLE 1

Examples of Inorganic Ion Content in Formation Water (g/ltr)

| Ion | Gulf of Mexico | Offshore Brazil | North Sea - north | North Sea - south |
|---|---|---|---|---|
| Sodium | 2-50 | 20-100 | 5-50 | 50-100 |
| Potassium | 0.1-1 | 1-5 | 0.1-1 | 1-5 |
| Magnesium | <0.1 | 0.1-1 | 0.1-1 | 1-5 |
| Calcium | 0.5-5 | 5-30 | 1-10 | 10-30 |
| Strontium | <0.1 | 1-5 | 0.1-1 | 0.1-2 |
| Barium | <0.1 | 0.1-1 | 0.1-1 | 0.1-1 |
| Chloride | 5-100 | 30-150 | 10-100 | 100-200 |

Figure 1:
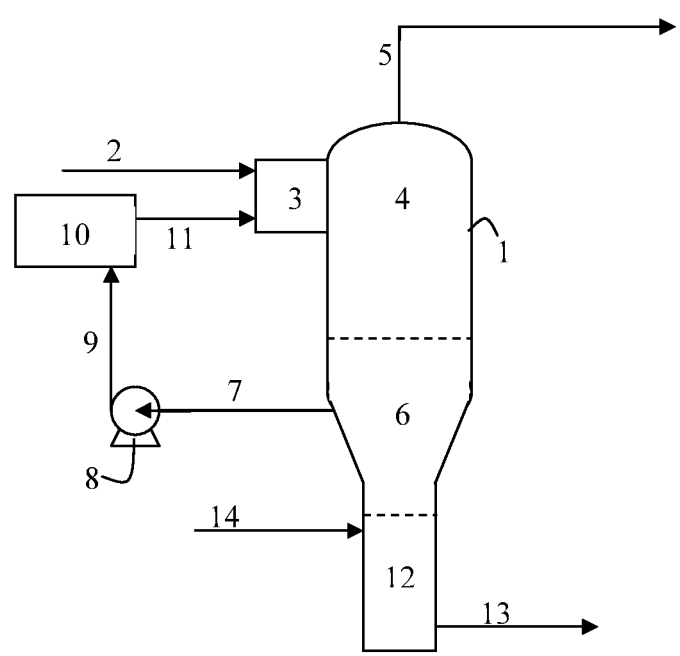
FIGS. 1 and 2 provide schematics of an apparatus and process of the invention.
Figure 2:
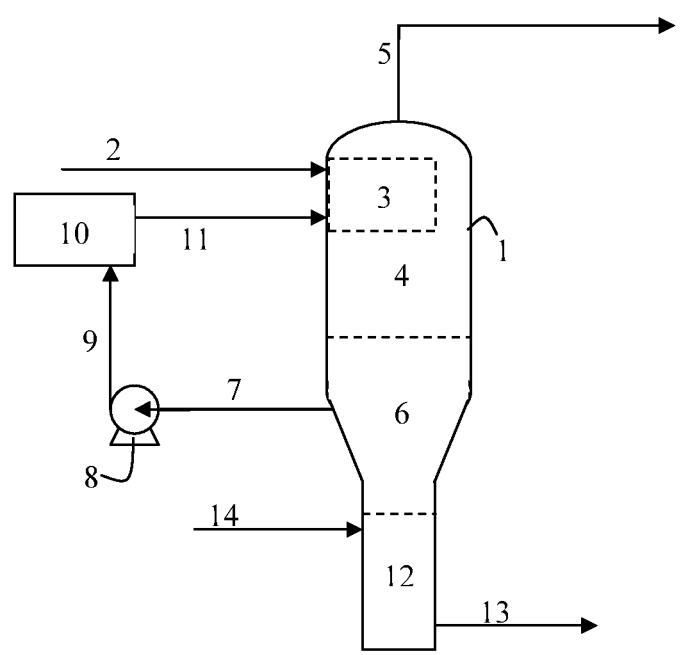

FIG. 1 and FIG. 2 depict a particular embodiment of this invention. In this embodiment, the process features a feed stream comprised substantially of a mixture of a) water, b) a process liquid that is miscible with water, has a density between 1.00 g/cc and 1.13 g/cc and has a boiling point of more than 150° C., and preferably more than 180° C., such as a glycol, and c) non-volatile contaminants. This flows through line 2 and enters mixing zone 3 in proximity to separation vessel 1. Alternatively the mixing zone 3 can be inside the separation vessel 1 as shown in FIG. 2. The normal operating pressure in separation vessel 1 is below atmospheric and preferably between 0.03 bara and 0.5 bara. A heated recycle fluid also enters mixing zone 3 through line 11 and upon mixing with the feed stream causes the vaporisation of volatile components contained in the feed stream including water and process liquid. In vapor separation zone 4 of the separation vessel 1, the vapor is separated from the non-volatile contaminants and other non-vaporised components of the mixture of recycle fluid and feed stream. The vapor leaves the separation vessel 1 through line 5 and flows to conventional processes downstream, such as condensing or distillation, which recover the process liquid for reuse. Liquid and non-volatile contaminants fall out of the vapor separation zone 4 into the liquid pool zone 6 of the separation vessel 1.

The liquid in the liquid pool zone 6 is comprised predominantly of oil or oil-like liquid components that: are less dense than water; are substantially non-miscible with water; and have a boiling point that is more than 40° C. higher, and preferably more than 100° C., higher than the boiling point of the process liquid. The total combined solubility of the non-volatile contaminants that fall into the liquid pool zone 6 is less than 10 wt % and preferably less than 1 wt % of the liquid therein. The total combined solubility of water, process liquid and non-volatile contaminants in the oil or oil-like liquid in the liquid pool zone 6 is less than 15 wt % and preferably less than 3 wt %. At normal operating conditions the oil or oil-like liquid is saturated with water, process liquid and non-volatile contaminants. Most or all of the non-volatile contaminants in the feed stream continuously precipitate, enter the liquid pool zone 6, and sink to the bottom.

Recycle fluid is drawn through line 7 from a part of the liquid pool zone 6 that is remote from any non-miscible substantial accumulation of water or process liquid, should any such accumulation exist. The liquid part of the recycle fluid is thereby comprised of more than 85 wt %, and preferably more than 97 wt %, of the oil or oil-like components described above. Pump 8 pumps the recycle fluid at a rate that is more than 10 times, and preferably more than 40 times, the feed stream flow rate, through line 9, through heat exchanger 10, and into mixing zone 3 through line 11. Sufficient heat is added to the recycle fluid in the heat exchanger 10 so that more than 90%, and preferably more than 99%, of the water and the process liquid in the feed stream are vaporised in the mixing zone 3. The amount of heat added by the heat exchanger 10 is sufficient to maintain a temperature in the liquid pool zone 6 that is higher than the boiling point of the process liquid and preferably more than 10° C. higher, at the prevailing conditions in the separation vessel 1. There is a sufficiently large mass of liquid in the liquid pool zone 6 at a sufficiently high temperature so that more than 95% and preferably more than 99% of any water and process liquid that falls into the liquid pool zone 6 will be vaporised. Most or all of any remaining water or process liquid that is not vaporised after entering the liquid pool zone 6 will settle towards the bottom of the liquid pool zone 6.

Connected to the bottom of or below the separation vessel 1 there is a stripping zone 12 that contains predominantly water. The oil or oil-like components of the liquid in the liquid pool zone 6, being substantially non-miscible with and less dense than water float on top of the water in the stripping zone 12. Non-volatile contaminants settle out of the liquid pool zone 6 and into the stripping zone 12. Many of these contaminants are highly soluble in water, such as sodium chloride, and will thereby cause the density of the water in the stripping zone 12 to rise. This rise in density further increases the separation forces that impede mixing between the liquid in the liquid pool zone 6 and the water in the stripping zone 12. At normal equilibrium conditions the water in the stripping zone 12 is saturated in non-volatile contaminants and the added amounts of these contaminants that fall out of the liquid pool zone 6 accumulate as solid matter in the stripping zone 12. The liquid at or near the bottom of the liquid stripping zone is optionally agitated periodically or continuously to break up lumps of solid matter and thereby assist with the separation of solid matter from liquid that has entered the stripping zone 12 from the liquid pool zone 6. A waste stream comprised predominantly of water and non-volatile contaminants is removed for disposal or further treatment through line 13 either periodically or continuously. Water is added through line 14 to maintain liquid levels in the apparatus and to optionally assist with the break up of lumps of solid matter, when waste is drawn out through line 13.

In this particular embodiment of the invention, the loss of process liquid in the waste stream in line 13 is minimised. For the example of a feed stream comprised of 40% to 90% mono-ethylene glycol, sufficient heat is transferred from the heated recycle fluid in line 11 to the feed stream in the mixing zone 3 to vaporise more than 90%, and preferably more than 99%, of the water and glycol in the mixing zone 3. Given that water is significantly more volatile than glycol, most of any residual non-vaporised liquid from the feed stream would be glycol. However, if more than 99% of this residual glycol then vaporises upon entering the hot liquid pool zone 6, this leaves less than 0.1%, and preferably less than 0.01%, of the original glycol content in the feed stream that could settle as a distinct liquid phase towards the bottom of the liquid pool zone 6. Advantageously, it has been found that under these conditions the oil or oil-like components in the liquid pool zone 6 form an effective deterrent to the formation of the calcium-glycol-chloride complexes described earlier. Furthermore the oil or oil-like components cause accumulations of solids present in the liquid pool to remain soft, mobile and slippery, which avoids problems of sticking or hardening into large lumps, which in turn assists the separation of process liquid from these solids. Advantageously, it has been found that the above helpful characteristics of the solid matter persist if the temperature is reduced to less than 60° C. even if calcium-MEG-chloride complex is formed.

Continuing with the glycol example, the residual glycol, if any exists, and the precipitated non-volatile contaminants settle downwards through progressively cooler and less agitated liquid in the liquid pool zone 6. This continues until they come into contact with the water in the stripping zone 12. The water in the stripping zone 12, under normal equilibrium conditions, becomes a brine that is saturated, or close to saturated, in non-volatile contaminants that have settled from the liquid pool zone 6 into the stripping zone 12 and dissolved into the water therein. The dissolved ion content raises the base density of the brine to over 1.19 g/cc which is higher than the density of any glycol that may have settled through the liquid pool zone 6. As disclosed in WO 05/102491A1, and incorporated herein by reference, this density difference is an effective deterrent to the downward movement of glycol through the brine. By comparison, most or all of the solid contaminants are denser than the brine and settle through all the liquid and fall to the bottom of the stripping zone 12 to be removed through line 13. If there is any glycol present most of it will tend to accumulate at the interface between the liquid pool zone 6 and the brine in the stripping zone 12. The glycol can be extracted periodically from this interface and pumped back into the feed stream to recover the glycol. In this way the glycol loss via the waste stream in line 13 can be further reduced to well below 0.1%.

In a further embodiment of the invention, most or all of any vaporised oil or oil-like components of the recycle fluid that leave the separation vessel 1 through line 5 are separated from the process liquid and water in downstream equipment and returned to the separation vessel 1.

In another embodiment of the invention, the temperature of the liquid in the liquid pool zone 6 is allowed to drop such that less process liquid is vaporised and more settles through the liquid pool zone 6 to reach the stripping zone 12. Furthermore in the case of a feed stream containing glycol contaminated with sodium, calcium, and chloride, the conditions near the bottom of the liquid pool zone 6 are allowed to change sufficiently to cause calcium-glycol-chloride complex to form and solidify. Advantageously, it has been found that when solid calcium-glycol-chloride complex compound falls into and mixes with the type of brine in the stripping zone 12, the glycol is preferentially stripped out leaving a waste solid that is separated from the glycol. This occurs because the glycol is infinitely miscible with water whereas the calcium and chlorides will not dissolve into the brine once the brine is saturated in these elements. The glycol contaminated brine can then be periodically extracted and mixed back into the feed stream to recover the glycol. This technique has been observed to recover more than 80% of the glycol that would otherwise remain bound into calcium-glycol-chloride complex compound.

Furthermore, when water is added through line 14 it can be done quickly. This agitates the fluids at the bottom of the liquid pool zone 6 and breaks up accumulations of solid matter to assist settling and separation of glycol from the solids.

The glycol recovery can be further improved if the stripping zone 12 is pressurised to about 2 bara. One way to do this is to pump the mixture of fluids and solids from the lower part of the liquid pool zone 6 to a mixing zone 12 that is in a separate vessel. The mixing zone 12 is not part of the separation vessel 1 and is thus able to operate at a higher pressure than separation vessel 1. This enables the temperature of the brine therein to remain above the melting point of the calcium-glycol-chloride complex compound without boiling. In these circumstances the glycol is not bound into solid calcium-MEG-chloride complex and is thereby easier to recover. It is also noted that the brine near the top of the stripping zone 12 absorbs most of the glycol, which in turn dissolves less salt than water and therefore has a slightly lower density than the brine below it which contains less glycol. Thus, there is a density gradient that impedes the descent of the glycol toward the bottom of the stripping zone 12. This effect is similar to that described in WO 05/102491A1. If the stripping zone 12 is more than 2 m tall, and preferably more than 4 m tall, then this becomes an effective means to further reduce the loss of glycol in the waste stream.

Example 1

Removal of Salts and Other Solids from Mono-Ethylene Glycol (MEG)

The following description presents an exemplification of how the method of the invention can be used in gas and oil processing facilities, as an improvement to the methods reported in U.S. Pat. No. 6,685,802 and WO 05/102491A1, for removing inorganic contaminants including those listed in Table 1 from aqueous solutions of mono-ethylene glycol (hereinafter termed MEG).

In this example, the primary component of the recycle fluid is an oil or oil-like liquid which has certain properties including:

substantially non-miscible with water
substantially non-miscible with MEG
thermally stable over the normal operating temperature range of 100 to 180° C.
normal boiling point above 300° C.
low viscosity at operating temperature
low capacity to dissolve the most commonly encountered inorganic non-volatile contaminants of MEG, including chlorides, oxides, bicarbonates and carbonates of sodium, potassium, calcium, magnesium and iron
density less than 0.95 g/cc when saturated with MEG and non-volatile contaminants at an operating temperature of 100 to 180° C.

Recycle fluids that have been observed to perform satisfactorily include mixtures of n-paraffin oils or waxes predominantly in the range from hexadecane to octacosane, and some oils generally known as heat transfer oils that are typically used in hot oil heating circuits. It is further expected that mixtures of the above and optionally with one or more additional components selected from a list comprising crude oil, mineral base oil, synthetic oil, hydrocracked base oil, middle distillates, fuel oil, diesel, and other liquids with suitable properties, will also perform satisfactorily.

The potential to use crude oils or fractions thereof as a part of the recycle fluid formulation is particularly attractive at locations where these fluids are produced in the same oil and gas production facility that operates the MEG regeneration process. These fluids typically contain a high fraction of high MW paraffins mixed with other more volatile components. At start-up the more volatile components may vaporise and leave the Flash Separator leaving behind a longer lasting less volatile liquid for continued operation of the process. The acceptability of this use of crude oil depends upon a case by case analysis of the composition of the crude oil under consideration and an assessment of its compatibility with MEG. If the crude oil proves to be acceptable then there would be further cost savings and higher reliability as there would be less reliance upon external sources to resupply the facility with recycle fluid.

It is further noted that the precautionary steps taken to minimise MEG oxidation and degradation during regeneration, including reduced temperature due to operation under vacuum, design and operation of the recycle fluid heating system in a manner that avoids high metal temperatures, and optional addition of oxygen scavenging agent, also reduce the risk of oxidation and degradation of the recycle fluid.

The typical properties of most of the above examples of oils to use as components of the 35 recycle fluid are: density less than 0.8 g/cc at 150° C.; vapor pressure less than 10% of that of MEG; viscosity less than 3 cP at 150° C.; substantially insoluble in water and MEG; compatible with and non-reactive with most common naturally occurring hydrocarbon fluids; and having a hazard profile is similar to that of many other substances encountered by personnel at oil and gas production facilities.

The operating pressure of the Flash Separator is maintained within a range from about 0.05 to 0.15 bara. The final boiling point of the feed stream approximately equals the boiling point of MEG, which, within the range of operating pressures noted above, is about 120° C. to 145° C. The recycle fluid is heated to 20 to 30° C. above the final boiling point of the feed stream and enters the Flash Separator through one or more tangential nozzles in the upper part of the vessel. The feed stream enters the Flash Separator through one or more nearby tangential nozzles. The recycle fluid flow rate is between 40 and 80 times the feed stream flow rate. When the two streams commingle, substantially all of the liquid content of the feed stream is vaporised while the recycle fluid, any residual liquid MEG, and precipitated solid particles spiral downwards against the wall of the vessel and enter the liquid pool. The upper part of the liquid pool is maintained at a temperature at least 10° C. above the final boiling point of the feed stream so that substantially all of any residual liquid MEG is rapidly vaporised upon entering the hot liquid pool.

Solid matter, which is mostly precipitated salt crystals of various types including sodium chloride and calcium chloride settle through the liquid pool, through a quiescent cooler zone of liquid in the lower part of the liquid pool below the recycle fluid draw-off point and out the bottom nozzle of the vessel. Upon dropping through this bottom nozzle the solid particles continue to settle by gravity through a vertical section of pipe which contains water and into a water-filled salt vessel connected to the bottom of the vertical pipe. The solids settle through and redissolve in the water until the water is saturated, after which they settle as solid mater that collects in the salt vessel. The mixture of solids and liquid at or near the interface between the liquid pool and the water is occasionally locally agitated so as to break up lumps of solid matter and assist the passage of finely divided solid matter into the water.

As the water dissolves the various salts its density rises to about 1.2 g/cc or higher. By comparison the density of any residual MEG that may have settled through the liquid pool will be no more than about 1.16 g/cc. The density of the water is thus significantly higher than that of both MEG and the liquid pool which is an effective barrier against the downward movement of either MEG or the recycle fluid into the salt vessel. The presence of MEG in the water below the interface with the liquid pool reduces the conductivity of the liquid at this point and this is measured by conductivity probes. When excessive MEG is detected the liquid containing the MEG is extracted and pumped back into the feed stream to recover the MEG. When a batch sized quantity of salt has been collected in the salt vessel and after residual MEG has been recovered, water is injected into the vertical pipe at the interface with the liquid pool. This added water initially has a density of about 1.0 g/cc, hence it will push the denser salt laden waste water out the bottom of the salt vessel.

The MEG-water vapour leaving the Flash Separator may contain a small fraction of vaporised recycle fluid. A number of conventional means are available to recover this fluid including condensing the vapor either in a condenser or in a distillation column and allowing the oil or oil-like condensed components to float in a separate layer on top of any condensed MEG and/or water and from there be pumped back to the Flash Separator. The equipment in this part of the process is similar to gravity separators used on many oil and gas production sites to separate hydrocarbons from aqueous liquids.

Example 2

Results for MEG

Table 2 below presents the results that have been observed experimentally when the process of the invention has been applied to separate dissolved sodium, calcium and chloride contaminants from MEG using two types of recycle fluid, one being a mixture of high MW n-paraffin hydrocarbons manufactured by Nippon Seiro Co Ltd, and the other a commercially available heat transfer oil manufactured by Petro-Canada.

TABLE 2

Experimental Results with Mono-ethylene Glycol

|  | Case 1: High MW n-paraffins | Case 2: Heat Transfer Oil |
|---|---|---|
| MEG content in feed stream | 80% | 80% |
| Inorganic Ion Content in feed stream | Na: 33 g/ltr<br>Ca: 11 g/ltr<br>Cl: 70 g/ltr | Na: 33 g/ltr<br>Ca: 11 g/ltr<br>Cl: 70 g/ltr |
| Operating pressure of separation vessel | 0.1 bara | 0.1 bara |
| Operating temperature of liquid pool | 145° C. | 145° C. |
| Type of solid matter formed | Chloride salts of sodium and calcium<br>No evidence of Ca-MEG-Cl complex | Chloride salts of sodium and calcium<br>No evidence of Ca-MEG-Cl complex |
| MEG content in Brine in Stripping Zone | <1 wt % | <1 wt % |
| MEG content in Waste Solids in Stripping Zone | <1 wt % | <1 wt % |

The results shown in Table 2 are a marked improvement on prior methods. In the methods as reported in U.S. Pat. Nos. 5,993,608, 6,340,373, 6,508,916 and 6,685,802, the loss of glycol is unavoidably high as the waste solid matter is withdrawn as part of a slurry or similar fluid in which the liquid part is concentrated glycol. Further equipment such as a settling tank, filter, or centrifuge is required to recover the glycol before disposing of the waste solids. The lowest cost of these, i.e. settling tank, is least effective in recovering glycol. For this reason, many plants that use flash vaporisation to treat glycol also add a centrifuge to reduce glycol losses to about 10 wt % of the waste solids. As can be seen from Table 2, the process disclosed herein shows a multi-fold reduction in glycol losses when compared to the performance of a centrifuge. Furthermore, a centrifuge is an expensive and complex item of equipment. The present invention avoids this cost and complexity.

The advantages of the present invention are also apparent when considering the removal of calcium. Based on the methods reported in U.S. Pat. Nos. 5,993,608, 6,340,373, 6,508,916 and 6,685,802, significant amounts of calcium and other similar divalent cations in the glycol feed stream can lead to severe problems. This is due to the formation of calcium-glycol-chloride complex compounds in the Flash Separator, unless additional treatments are used. According to prior methods, the calcium is removed by injection of carbonate ions into the feed stream upstream of the flash vaporisation process to promote precipitation of calcium carbonate followed by clarification and/or filtration to remove the calcium carbonate. The carbonate is typically injected in the form of an aqueous sodium carbonate solution, meaning that non-volatile contaminants (i.e. sodium and carbonate) are being added which must then be extracted along with the calcium.

For this previous procedure, an excess of carbonate is normally injected to ensure that all the calcium is precipitated in a timely manner. Thus, the amount of solid matter to remove in the clarifiers and/or filters is over 2.5 times the original amount of calcium in the feed stream. This leads to added loss of glycol with the waste material from the clarifiers and/or filters. There is also considerable uncertainty in knowing exactly how much calcium is in the feed stream, and the calcium content can change unpredictably. This uncertainty can lead to further overdosing with sodium carbonate, which compounds the problem of glycol losses. The net outcome is that removal of calcium using the prior methods can be expected to result in glycol losses that exceed 30% of the original calcium content. In addition, more energy is needed to vaporise the added water in the sodium carbonate solution.

The present invention thus represents a significant improvement over the prior methods used to remove calcium and similar divalent cations because glycol losses are significantly lower and there is no need for the sodium carbonate dosing system, clarifiers or filters.

The examples described herein are for purposes of illustrating embodiments of the invention. Other embodiments, methods, and types of analyses are within the scope of persons of ordinary skill in the art and need not be described in detail herein. Other embodiments within the scope of the art are considered to be part of this invention. Furthermore, titles, headings, or the like are provided to enhance the reader's comprehension of this document, and should not be read as limiting the scope of the present invention.

The entire disclosures of all patent applications, patents, and publications, cited above and below, if any, are hereby incorporated by reference in their entirety.

Throughout this specification, and any sections which follow, unless the context requires otherwise, the words "comprise," "comprising" and the like, are to be construed in an inclusive sense as opposed to an exclusive sense, that is to say, in the sense of "including, but not limited to".

What is claimed is:

1. A method of extracting solids, which are dissolved or undissolved, from a feed stream comprising a mixture of water, a process liquid, and the solids to be extracted, the method comprising the steps of:
   a) placing an oil recycle liquid that is less dense than water, and is comprised of components that are substantially non-miscible with and less volatile than water and less volatile than the process liquid, into a separation vessel;
   b) introducing the feed stream into a mixing zone in proximity to or within the separation vessel;

c) rapidly vaporising volatile components of the feed stream upon mixing the feed stream with the recycle liquid in the mixing zone, thereby causing the precipitation of the dissolved or undissolved solids to be extracted;

d) conveying the mixture of the feed stream and the recycle liquid, including the vaporised components and the precipitated solids, into a separation zone within the separation vessel;

e) conveying the vaporised components out of the separation zone and out of the separation vessel, thereby leaving behind a remaining mixture of the unvaporised liquid components and the precipitated solids and undissolved solids that falls into and is collected in a substantially liquid pool in a lower portion of the separation vessel;

f) drawing the recycle liquid from the substantially liquid pool at a rate that is more than ten times a feed stream flow rate;

g) pumping the recycle liquid through a heat exchanger;

h) supplying sufficient heat to the recycle liquid in the heat exchanger such that the amount of heat added to the recycle liquid is sufficient to cause the vaporisation of more than 99% of the volatile components of the feed stream when the recycle liquid and the feed stream are mixed within or in proximity to the separation zone;

i) allowing at least a portion of the precipitated solids in the substantially liquid pool and at least a portion of any liquid bound thereto to move into a stripping zone and come into contact with water contained therein;

j) allowing at least a portion of the precipitated solids that has moved into the stripping zone to move through at least a portion of the water in the stripping zone;

k) wherein the passage of the portion of precipitated solids through the portion of the water displaces at least a portion of any liquid bound to the portion of the precipitated solids; and l) removing from the stripping zone a waste aqueous stream comprising at least a portion of the precipitated solids that have moved into the stripping zone.

2. The method as claimed in claim 1 wherein some or all vaporised components of the recycle liquid are condensed and returned to the liquid pool in the lower portion of the separation vessel.

3. The method as claimed in claim 1 wherein the stripping zone is connected to the bottom of the separation vessel and at least a portion of the precipitated solids from the liquid pool fall by gravity out of the liquid pool and into the stripping zone.

4. The method as claimed in claim 1 wherein water is added to the stripping zone to displace the waste aqueous stream.

5. The method as claimed in claim 1 wherein the separation vessel is operated at a pressure between 0.03 and 0.60 bara to avoid thermal degradation of thermally sensitive process fluids.

6. The method as claimed in claim 1 wherein the process liquid is mono-ethylene glycol.

* * * * *